(12) United States Patent
Sasaki et al.

(10) Patent No.: US 8,315,820 B2
(45) Date of Patent: Nov. 20, 2012

(54) POTENTIOMETRIC TITRATION METHOD AND POTENTIOMETRIC TITRATION APPARATUS

(75) Inventors: Masahiro Sasaki, Kanagawa-ken (JP); Toshiyuki Kamo, Kanagawa-ken (JP); Yoko Ohashi, Kanagawa-ken (JP)

(73) Assignee: Mitsubishi Chemical Analytech Co., Ltd., Yokkaichi-shi, Mie-ken (JP)

( * ) Notice: Subject to any disclaimer, the term of this patent is extended or adjusted under 35 U.S.C. 154(b) by 429 days.

(21) Appl. No.: 12/705,214

(22) Filed: Feb. 12, 2010

(65) Prior Publication Data

US 2010/0191479 A1 Jul. 29, 2010

(30) Foreign Application Priority Data

Oct. 23, 2008 (JP) ................... 2008-272855

(51) Int. Cl.
*G01N 31/00* (2006.01)
(52) U.S. Cl. .......................................................... 702/25
(58) Field of Classification Search ................. 702/25
See application file for complete search history.

(56) References Cited

U.S. PATENT DOCUMENTS 6,913,930 B2 * 7/2005 Bevan et al. .................. 436/163

FOREIGN PATENT DOCUMENTS

FR 2 504 680 10/1982

OTHER PUBLICATIONS

Extended European Search Report in EP 10 00 1360 dated Jun. 29, 2010.
Isbell, Jr., et al, "Computer Analysis of Data from Potentiometric Titrations Using Ion-Selective Indicator Electrodes", Analytical Chemistry, vol. 45, No. 14, Dec. 1973, pp. 2363-2369; XP-002585576.
Wu et al, "Versatile Microcomputer-Controlled Titrator", Analytical Chemistry, vol. 50, No. 14, Dec. 1978, pp. 2090-2098; XP-002585577.
Kamakura, "A Plot of the pH vs. the Logarithm of the Titrant Volume . . . ", Bull. Chem. Soc. Jpn., 53, 658-660 (1980), [vol. 53, No. 3]; XP-002585578.

* cited by examiner

*Primary Examiner* — Stephen Cherry
(74) *Attorney, Agent, or Firm* — Nixon & Vanderhye P.C.

(57) ABSTRACT

A potentiometric titration method including calculating a titration curve and a differential curve from measured values; computing a straight line (D) connecting the two measured values on the titration curve which are present adjacent to a tentative terminal point (P); computing a first estimation line (B1) and a second estimation line (B2) by a least squares method based on a set of the measured values (d1), (d2) and (d3) and a set of the measured values (d4), (d5) and (d6), respectively, on the titration curve, which are respectively spaced by a predetermined level apart from the tentative terminal point (P) by using the number of decision points (n) as an index where the number of decision points (n) represents the number of measured values on the previously set titration curve; computing an intermediate line (C) between the first estimation line (B1) and the second estimation line (B2); and computing an intersection point (A) of the intermediate line (C) and the straight line (D) to read out a value of the intersection point on an abscissa axis as a terminal point (a) of the titration.

4 Claims, 7 Drawing Sheets

POTENTIOMETRIC TITRATION METHOD AND POTENTIOMETRIC TITRATION APPARATUS

BACKGROUND OF THE INVENTION

The present invention relates to a potentiometric titration method and a potentiometric titration apparatus, and more particularly, to a potentiometric titration method capable of accurately determining a terminal point of titration irrespective of occurrence of change in indicator potential, and a potentiometric titration apparatus for performing automatic titration according to the potentiometric titration method.

Figure 7:
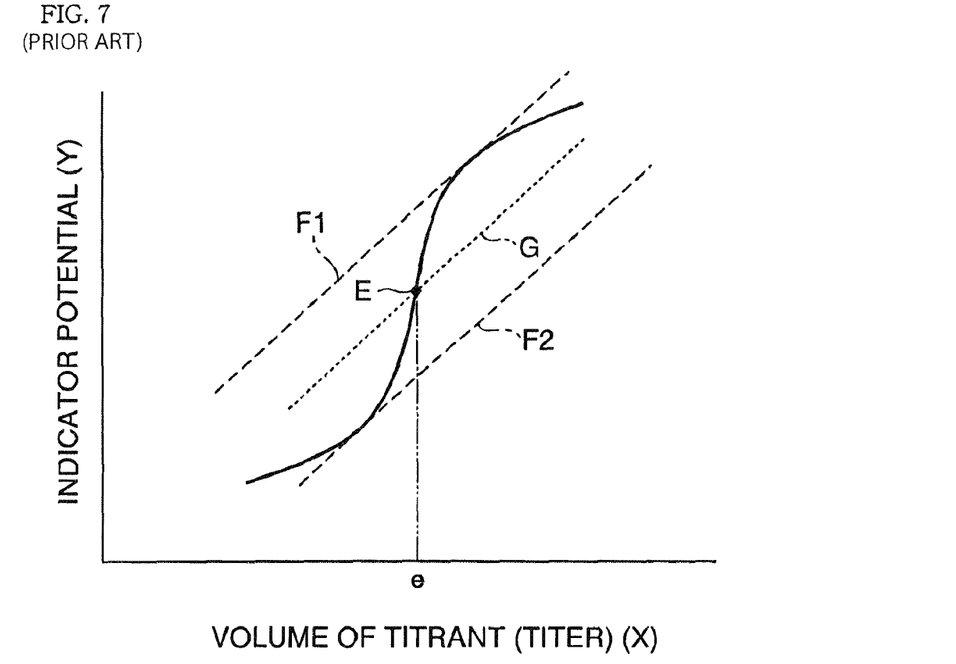
FIG. 7 is a graph showing a concept of the conventional potentiometric titration method using an intersection point method.

In the potentiometric titration analysis, there has been generally utilized an inflection point method or an intersection point method using a titration curve, or a method using a differential curve derived from the titration curve. FIG. 7 is a graph showing a concept of the conventional potentiometric titration analyzing method using the intersection point method, whereas FIG. 8 is a graph showing a concept of the conventional potentiometric titration analyzing method using the differential curve.

In the above inflection point method, the titration procedure is carried out to prepare a titration curve in which the value (Y) of indicator potential is plotted on an ordinate axis and the value (X) of a volume of a titrant added to a sample is plotted on an abscissa axis to determine the abscissa axis value corresponding to an inflection point thereof as a terminal point of the titration. The inflection point method is suitably used for the analysis in which an inflection point is apparently observed. Also, in the intersection point method, as shown in FIG. 7, tangent lines (F1) and (F2) each having a gradient of 45° are drawn at the portions of a titration curve prepared in the same manner as described above which portions extend toward maximum and minimum values thereof, respectively, and then an intermediate line (G) which is spaced by an equal distance from each of the tangent lines and extend in parallel therewith is drawn, to thereby read an abscissa axis value of an intersection point (E) between the titration curve and the intermediate line (G) as a terminal point (E) of the titration. The intersection point method is a so-called drawing method and effective for the analysis of a titration curve having a pattern in which any clear inflection point is hardly recognized.

Figure 8:
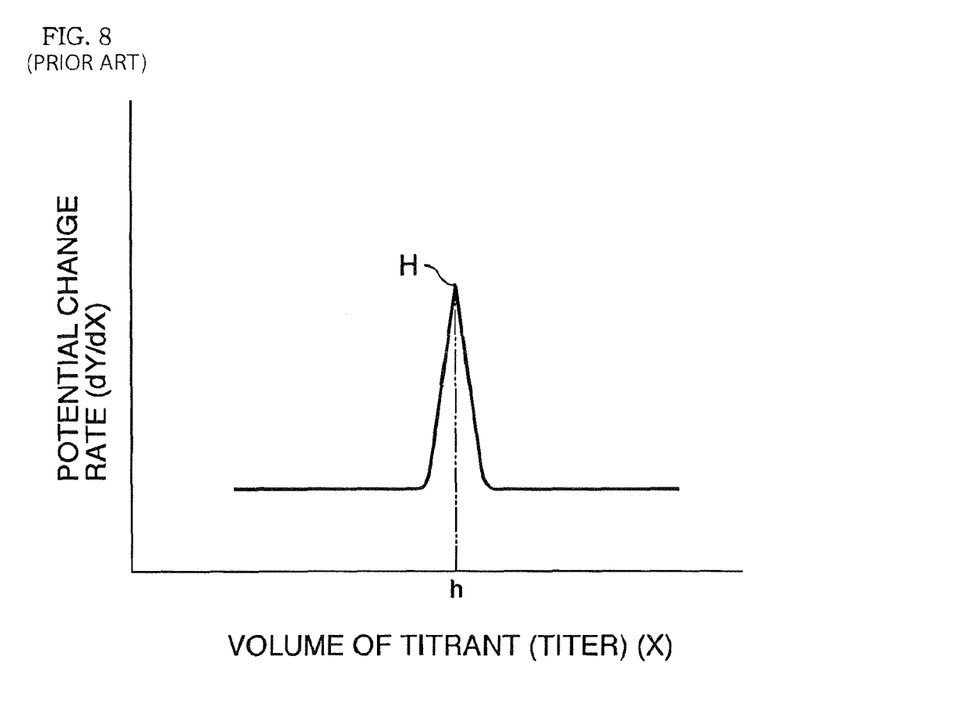
FIG. 8 is a graph showing a concept of the conventional potentiometric titration method using a differential curve.

On the other hand, in the method using a differential curve, as shown in FIG. 8, an absolute value of a rate of change in potential (dY/dX) is plotted on an ordinate axis and the value (X) of a volume of a titrant added is plotted on an abscissa axis to prepare a differential curve, and the abscissa value of a peak (H) on the differential curve at which the rate of change in potential (dY/dX) becomes maximum is read out as a terminal point (h) of the titration. The method using a differential curve is suitably used for automatic titration in which automatic computation is carried out using a titration apparatus (refer to JIS K0113, 1997, Revised Edition "General Rules for methods of potentiometric, amperometric, coulometric and Karl Fischer titrations").

Meanwhile, in the titration analysis, a titration curve is generally prepared by plotting about 10 to 20 measured values to determine the above inflection point, intersection point or peak on the curve. However, owing to the problems such as properties of the sample to be measured and poor measuring sensitivity of the apparatus, it has been difficult to obtain a smooth titration curve. Also, in the case where there is caused considerable change in indicator potential at an inflection point portion of the titration curve such as a long-continued maximum gradient portion of the curve including the inflection point, or in the case where a peak of the differential curve is unclear, there tends to occur such a problem that a terminal point of the titration curve cannot be accurately determined. When the titration curve is graphed to manually draw the tangential lines, an analysis accuracy of the titration analysis may be enhanced by skilled experts to a certain extent. However, in particular, when performing an automatic titration using a titration apparatus, it has been still difficult to estimate a smooth titration curve and therefore estimate adequate tangential lines.

SUMMARY OF THE INVENTION

The present invention has been accomplished in view of the above conventional problems. An object of the present invention is to provide a potentiometric titration method capable of accurately determining a terminal point of titration irrespective of occurrence of change in indicator potential which is also suitable for automatic titration, and a potentiometric titration apparatus for performing automatic titration according to the potentiometric titration method.

To solve the above problem, in accordance with the present invention, in the case of assuming a titration curve and a differential curve, a tentative terminal point of titration is set on the titration curve using a peak of the differential curve; measured values on the titration curve which are spaced a sufficient distance apart from the tentative terminal point, more specifically, three measured values which are not present in the vicinity of an inflection point of the titration curve and constitute respective portions of the titration curve extending toward maximum and minimum values thereof where the change in indicator potential is moderate, are used as decision points, to determine a linear estimation line for each set of the decision points; and an intersection point between an intermediate line of these estimation lines and the titration curve is adopted as a terminal point of the titration. By using such a method, it is possible to avoid adverse influence due to a large change in indicator potential in the vicinity of the inflection point, and to perform automatic titration by automatic computation.

That is, in a first aspect of the present invention, there is provided a potentiometric titration method for conducting titration based on an amount of a titrant added (titer) and an indicator potential, the method including the steps of:

calculating a continuous line prepared by plotting a value (Y) of the indicator potential on an ordinate axis and plotting a value (X) of a volume of the titrant on an abscissa axis, as a titration curve, the values (X) and (Y) being determined according to the titration procedure;

calculating a continuous line prepared by plotting an absolute value of a rate of change in potential (dY/dX) on an ordinate axis and plotting the value (X) of a volume of the titrant on an abscissa axis, as a differential curve;

calculating a value on the titration curve which corresponds to a peak (P1) on the differential curve, as a tentative terminal point (P);

computing, on a computer, a straight line (D) connecting two measured values on the titration curve which are present adjacent to the tentative terminal point (P);

computing, on a computer, a linear first estimation line (B1) by a least squares method based on measured values (d1), (d2) and (d3) on the titration curve which are present in the range of from [(tentative terminal point (P))−(number of decision points (n))] to [(tentative terminal point (P))−(number of decision points (n))+2], and computing, on a computer, a linear second estimation line (B2) by a least squares method based on measured values (d4), (d5) and (d6) on the titration curve which are present in the range of from [(tentative terminal point (P))+(number of decision points (n))−2] to [(tentative terminal point (P))+(number of decision points (n))] wherein the number of decision points (n) represents the number of the measured values on portions of the titration curve previously set and used for determination of a terminal point of the titration (with the proviso that the number of the measured values are not less than 3 in each of the portions of the titration curve which extend in positive and negative directions, respectively, along the abscissa axis, on the basis of the tentative terminal point (P) as a reference point);

computing, on a computer, an intermediate line (C) between the first estimation line (B1) and the second estimation line (B2); and computing, on a computer, an intersection point (A) of the intermediate line (C) and the straight line (D) to read out a value of the intersection point on the abscissa axis as a terminal point (a) of the titration.

Also, in a second aspect of the present invention, there is provided a potentiometric titration apparatus including a titration vessel accommodating a sample, a detector for detecting a indicator potential using an indicator electrode and a reference electrode, a titration section constituted from a titrant addition device for adding a titrant to the sample, and a control section for controlling the titrant addition device based on the indicator potential detected by the detector and computing a terminal point of titration, where the control section has a function of computing the terminal point of titration according to the potentiometric titration method as defined above.

EXPLANATION OF REFERENCE NUMBERS

1: Titration section; 2: Control section; 3: Display/Recording section; 4: Titration vessel; 5: Detector; 51: Indicator electrode; 52: Reference electrode; 6: Titrant addition device; A: Intersection point; a: Terminal point; B1: First estimation line; B2: Second estimation line; C: Intermediate line; D: Straight line; d1 to d6: Measured values (decision points (plot points)); L: Threshold value; P1: Peak; P: Tentative terminal point; V1, V2: Regions of values of indicator potential.

DETAILED DESCRIPTION OF THE INVENTION

Figure 1:
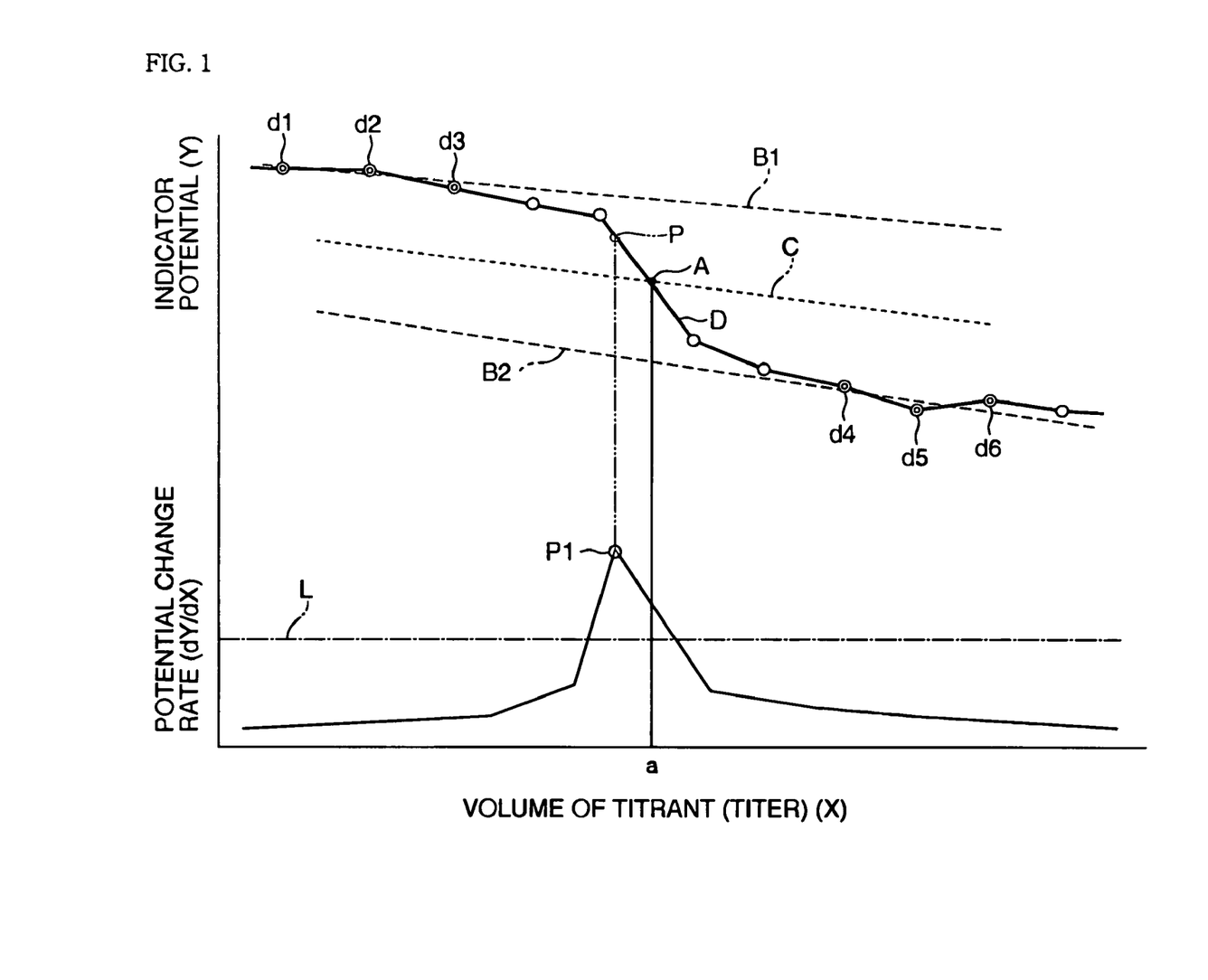
FIG. 1 is a graph visually showing a concept of a potentiometric titration method according to the present invention.
Figure 2:
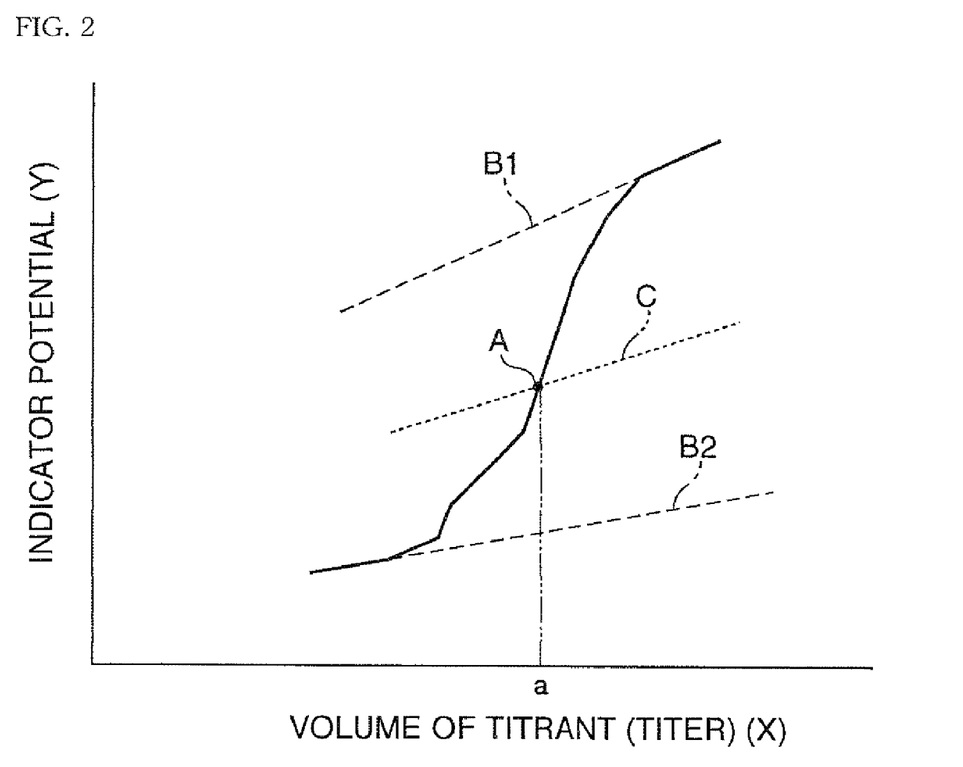
FIG. 2 is a graph showing an example of application of the present invention to titration analysis including a plurality of reactions.
Figure 3:
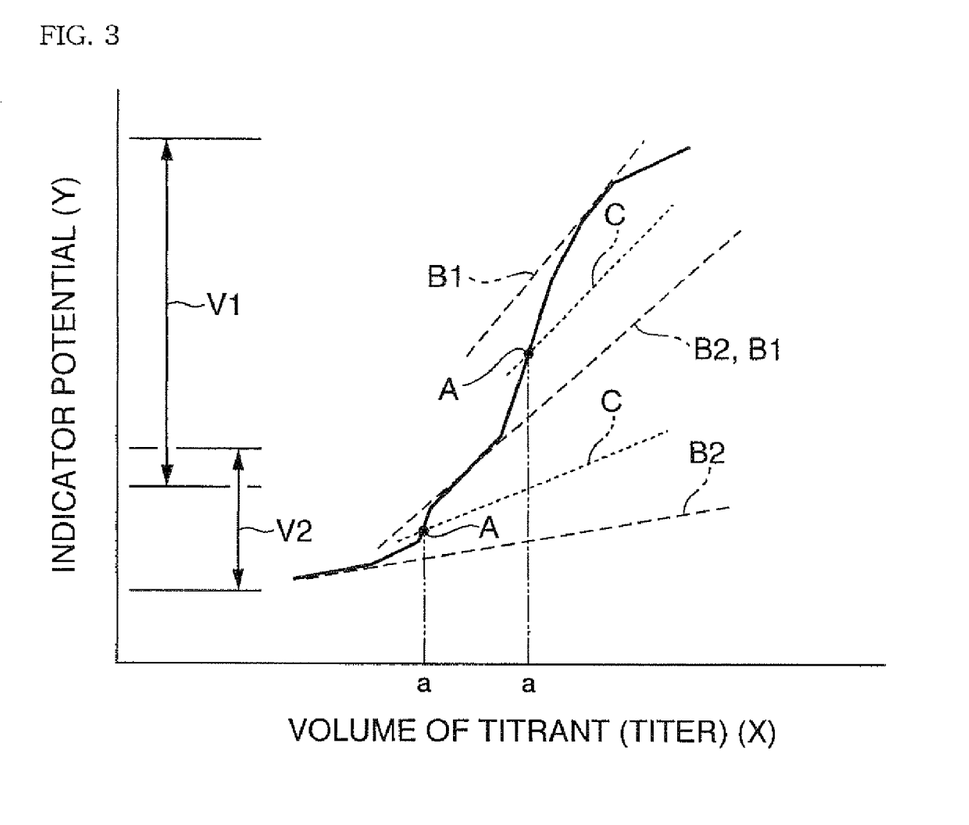
FIG. 3 is a graph showing another example of application of the present invention to titration analysis including a plurality of reactions (inflection points).
Figure 4:
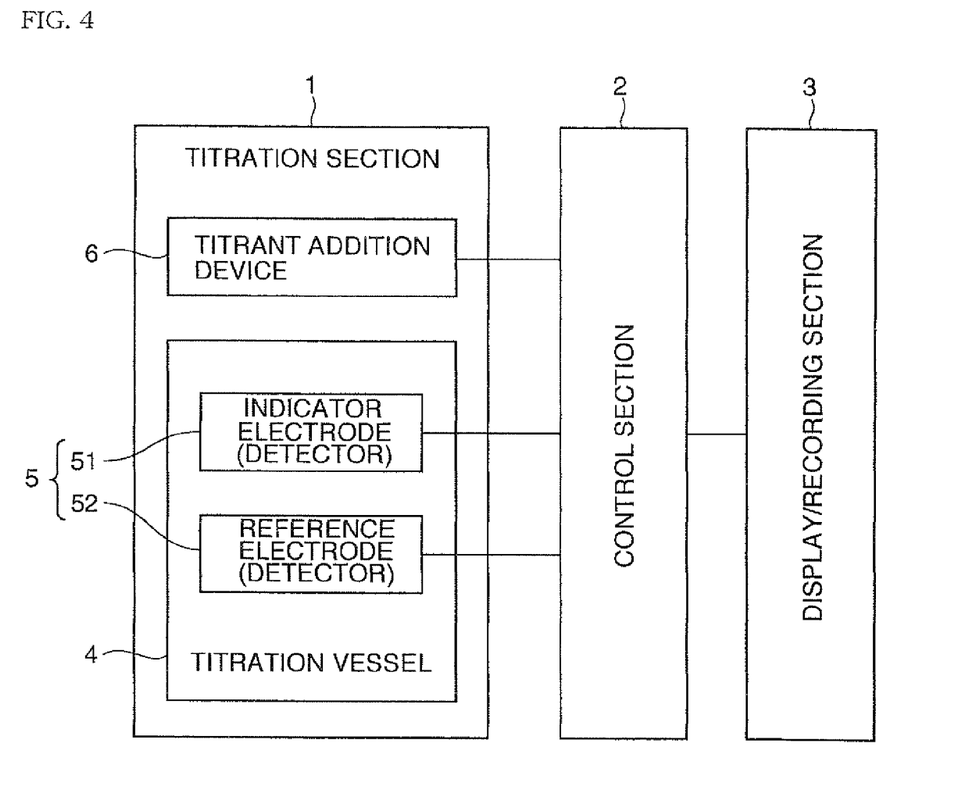
FIG. 4 is block diagram showing a basic construction of a potentiometric titration apparatus according to the present invention.
Figure 5:
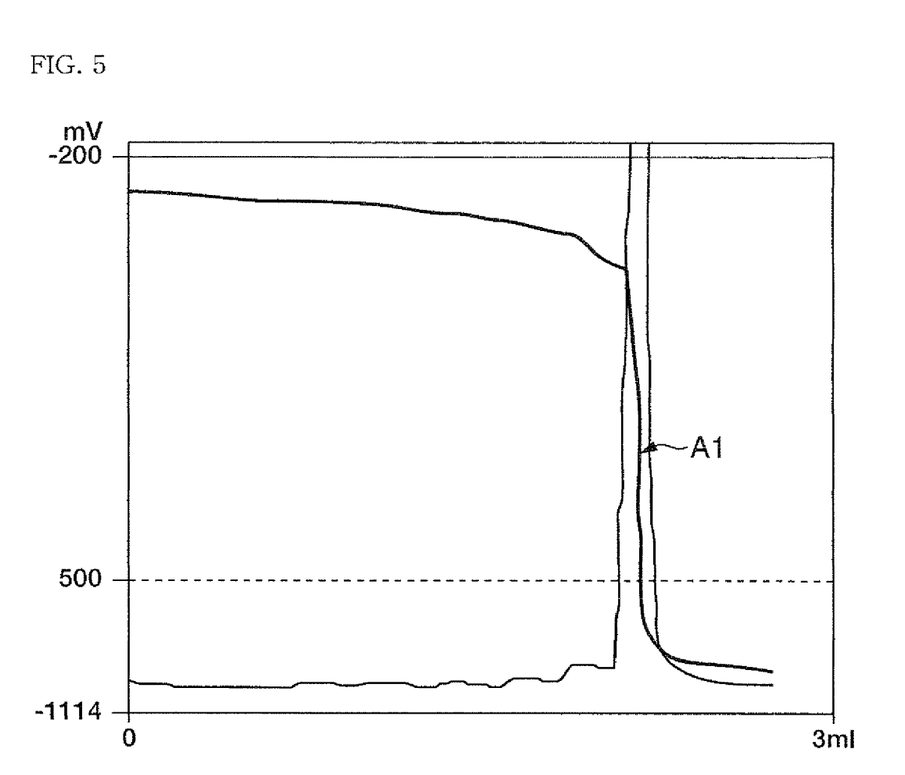
FIG. 5 is a view showing an image displayed in oxidation-reduction reaction as one embodiment of the present invention.
Figure 6:
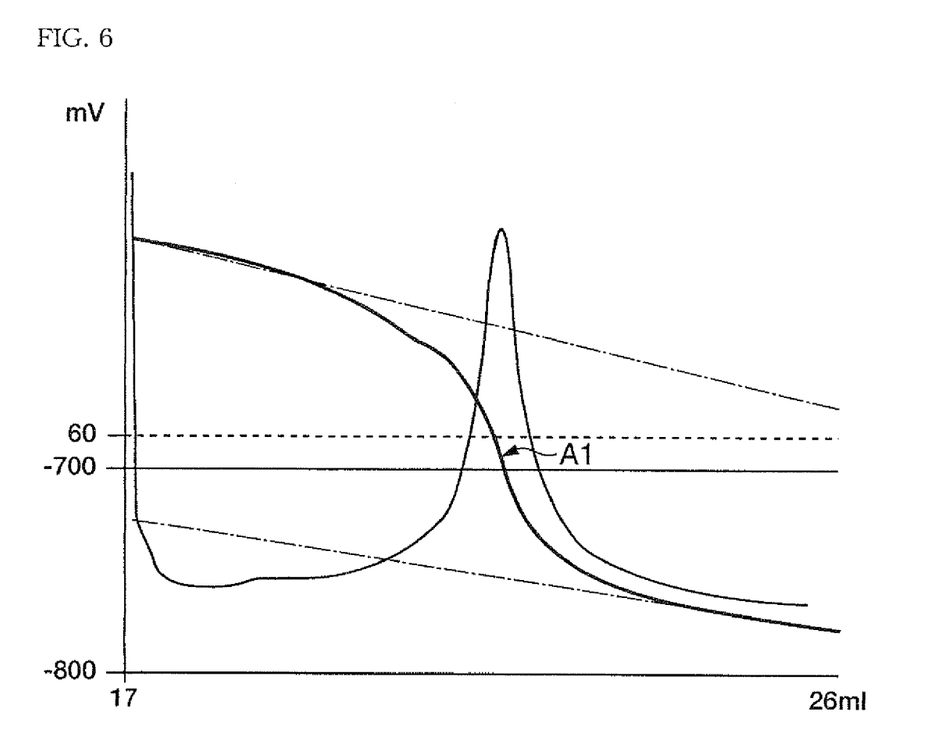
FIG. 6 is a view showing an image displayed in analysis of a purity of caffeine as another embodiment of the present invention.

The embodiments of the present invention are described by referring to the accompanying drawings in which FIG. 1 is a graph showing a concept of a potentiometric titration method according to the present invention; FIGS. 2 and 3 are graphs showing examples of application of the present invention to titration analysis including a plurality of reactions; FIG. 4 is block diagram showing a basic construction of an potentiometric titration apparatus according to the present invention; and FIGS. 5 and 6 are views showing images displayed in titration analysis as respective embodiments of the present invention.

The present invention can be applied to titration for determining neutralization, oxidation-reduction, precipitation, photometric, electric conductivity, polarization, petroleum neutralization value, stat, etc., by suitably selecting thee kind of electrodes used in the detector and a titrant. First, the potentiometric titration apparatus according to the present invention is explained. As shown in FIG. 4, the potentiometric titration apparatus according to the present invention is constructed from the same mechanical constitutional elements as used in the conventionally known apparatuses, and generally comprises a titration section (1), a control section (2) and a display/recording section (3).

The titration section (1) comprises a titration vessel (4) for accommodating a sample, a detector (5) for detecting an indicator potential using an indicator electrode (51) and a reference electrode (52), and a titrant addition device (6) for adding a titrant to the sample. The titration vessel (4) is constructed from a glass container mounted on a stirrer.

The detector (5) is equipped with at least one pair of the indicator electrode (51) and the reference electrode (52). As the indicator electrode (51), there may be used various metal electrodes capable of responding to a metal ion concentration, membrane electrodes capable of converting a difference in concentration between inside and outside of a membrane into a potential, and glass electrodes. Also, as the reference electrode (52) providing a reference potential, there may be usually used a salt bridge and a hardly-soluble metal salt electrode. The titrant addition device (6) is capable of controlling a titer by a pulse motor in proportion to a voltage detected by the indicator electrode (51), and comprises a burette having a tip inserted into the titration vessel (4) from which a titrant is dropped.

The control section (2) comprises a microcomputer into which a program is previously written, and a control circuit for controlling the titration section (1). More specifically, the microcomputer of the control section (2) comprises a logic board on which a processor (CPU), a main memory for computation (RAM), a program storing memory, a controller, an input/output device (I/O), etc., are mounted, and has a function of controlling the above control circuit according to progress of the titration. On the other hand, the control circuit is constructed of a circuit for monitoring signals detected by the indicator electrode (51) and the reference electrode (52) (electrode monitoring circuit), a circuit for controlling a dropping speed of the titrant from the titrant addition device (6), etc.

The control section (2) is constructed such that a control signal supplied from the microcomputer is outputted to the control circuit on the basis of the instruction generated from a control panel (not shown) to thereby control operation of the titration in the titration section (1) via the control circuit. In addition, the control section (2) is constructed such that a signal detected by the titration section (1) is inputted to the microcomputer via the control circuit to analyze data of the titration and output the analyzed results, if required, together with the analyzing process, to the display/recording section (3). Thus, the control section (2) has a function of controlling the titrant addition device (6) on the basis of an indicator potential detected by the detector (5) and computing a terminal point of the titration as described below.

The display/recording section (3) comprises a display for displaying a progress of the analysis and analysis results, and, if required, a small-size printer for printing the analysis results. Thus, the display/recording section (3) is constructed so as to display or record the terminal point of the titration as well as, if required, the indicator potential or the amount of the titrant added.

Next, the potentiometric titration method for performing potentiometric titration from an amount of a titrant added (titer) and an indicator potential according to the present invention is explained as a function of the above control section (2).

In the present invention, the value (Y) of the indicator potential detected by the detector (5) and the value (X) of a volume of the titrant added which values have been procured in the titration procedure are subjected a predetermined data processing to obtain an accurate terminal point of the titration. Meanwhile, in the following descriptions, for the sake of clear understanding, reference is made to graphs. However, in the present invention, since the terminal point of the titration can be determined by computation, preparation of the graphs is not necessarily required during the computation.

In the present invention, as shown in FIG. 1, a continuous line (bending line) prepared by plotting the value (Y) of the indicator potential on an ordinate axis and plotting the value (X) of a volume of the titrant on an abscissa axis is assumed as a titration curve (refer to an upper portion of the graph shown in FIG. 1), and further a continuous line (bending line) prepared by plotting an absolute value of a rate of change in potential (dY/dX) on an ordinate axis and plotting the value (X) of a volume of the titrant on an abscissa axis is assumed as a differential curve (refer to a lower portion of the graph shown in FIG. 1). In addition, the value on the titration curve which corresponds to a peak (P1) on the differential curve is assumed as a tentative terminal point (P).

In the titration analysis, in the case of a single reaction, one peak (P1) is determined on the differential curve to attain one terminal point. At this time, there may occur such a case where a plurality of peaks are observed on the differential curve. Therefore, on the basis of the tendency expected according to substances to be reacted or the tendency obtained during the titration analysis, a lower value (L) of an absolute value of the rate of change in potential (dY/dX) is set to extract such a peak (P1) on the differential curve at which the rate of change in potential (dY/dX) becomes maximum beyond the lower value. The value on the titration curve which corresponds to the above peak (P1) is determined as the tentative terminal point (P).

Next, the computation is carried out by using measured values constituting the titration curve. More specifically, the two measured values on the titration curve which are adjacent to the above tentative terminal point (P) are selected to compute a straight line (D) (linear function) connecting the two measured values. Such a straight line (D) is a line passing trough an inflection point on a titration curve, or a line located very closely to the inflection point when the titration curve is actually prepared.

In addition to the computation for preparing the straight line (D), measured points on the titration curve which are used for deciding the terminal point of the titration, are determined to compute two lines, i.e., a linear estimation lines (B1) and (B2) (linear functions). More specifically, the number of measured values on the titration curve is previously set as the number of decision points (n). The number of the decision points (n) may vary depending upon the number of data, and is usually 5 to 10 in each of forward and rearward directions from the inflection point on the titration curve from the practical viewpoints. However, in order to reduce adverse influence owing to a large change in the indicator potential in the vicinity of the inflection point, the number of the measured values which are used as the number of the decision points (n) is not less than 3 in each of the positive and negative directions along the abscissa axis on the basis of the tentative terminal point (P) as a reference point.

As the measured values (decision points) on the titration curve which are used for decision of the terminal point, there may be used two sets of values, i.e., a set of measured values (d1), (d2) and (d3) on the titration curve which are present in the range of from [(tentative terminal point (P))−(number of decision points (n))] to [(tentative terminal point (P))−(number of decision points (n))+2] (three measured values indicated by a double circle (◉) on the left side of the tentative terminal point (P) in FIG. 1), and a set of measured values (d4), (d5) and (d6) on the titration curve which are present in the range of from [(tentative terminal point (P))+(number of decision points (n))−2] to [(tentative terminal point (P))+(number of decision points (n))] (three measured values indicated by a double circle (◉) on the right side of the tentative terminal point (P) in FIG. 1). FIG. 1 illustrates thee case where the number of the decision points (n) is 5.

The first estimation line (B1) is computed by a least squares method on the basis of the measured values (d1), (d2) and (d3) on the titration curve which are present in the range of from [(tentative terminal point (P))−(number of decision points (n))] to [(tentative terminal point (P))−(number of decision points (n))+2]. Whereas, the second estimation line (B2) is computed by a least squares method on the basis of the measured values (d4), (d5) and (d6) on the titration curve which are present in the range of from [(tentative terminal point (P))+(number of decision points (n))−2] to [(tentative terminal point (P))+(number of decision points (n))]. The above first estimation line (B1) and second estimation line (B2) are similar to a tangential line as defined the conventional JIS methods. However, by using data sufficiently spaced apart from the inflection point and estimating a tendency of an unchanged portion of the titration curve by a least squares method, it is possible to accurately determine a range of the inflection point.

As described above, after computing the estimation lines (B1) and (B2), the intermediate line (C) of the first estimation line (B1) and the second estimation line (B2) are computed. The intermediate line (C) is a line (linear function) that extends spaced by an equal distance apart from each of the estimation lines (B1) and (B2). Then, the intersection point (A) of the intermediate line (C) and the above straight line (D) is computed, and the read-out value of the intersection point on an abscissa axis is determined as a terminal point (a) of the titration.

Thus, in the present invention, the tentative terminal point (P) on the titration curve is set by utilizing the peak (P1) on the differential curve, and 2 sets of the measured values on the titration curve which are spaced by a sufficient distance from the tentative terminal point, i.e., a set of the three measured points (d1) to (d3) and a set of the three measured points (d4) to (d6) which are respectively spaced from the inflection point of the titration curve and constitute portions of the titration curve extending toward maximum and minimum values where the change in potential is moderate, are used as decision points to determine the linear estimation lines (B1) and (B2) for each set of the decision points by a least squares method. Further, the intersection point between the intermediate line (C) of these estimation lines and the titration curve, more specifically, the intersection point (A) between the intermediate line (C) and the straight line (D), is adopted as a terminal point of the titration. Therefore, in accordance with the present invention, it is possible to accurately determine the terminal point of the titration without undergoing adverse influence owing to large change in the indicator potential in the vicinity of the inflection point. In addition, since the terminal point of the titration is simply computed according to a program set previously, the present invention can be suitably used for automatic titration.

The above embodiment of the present invention provides an example of titration including a single reaction. However, as shown in FIGS. 2 and 3, the present invention can also be similarly applied to other titration procedures, for example, titration including a two-stage reaction. FIG. 2 shows an example of titration analysis in which the titration curve is generally observed in the form of a quintic curve. In the titration analysis, in the case of determining one terminal point, the amount of the titrant added from a tip of the burette of the titrant addition device (6) is increased at predetermined proportions, and the number of the decision points (n) is also increased, so that the titration curve can be handled in the same manner as a cubic curve to obtain one terminal point (a).

Further, FIG. 3 shows an example of titration analysis in which the titration curve is observed in the form of a quintic curve similarly to FIG. 2. In the titration analysis, in the case of determining two terminal points, the range of the value (Y) of the indicator potential in which it is expected to observe any inflection points on the titration curve, is divided into a plurality of regions, for example, two regions (V1) and (V2). In each of the regions (V1) and (V2), the same computation as used above for the titration including a single reaction is carried out. In this case, the number of the decision points (n) for computation of each region may be set to a similar number to that used above for the titration including a single reaction. As a result, it is possible to determine a plurality of terminal points, for example, two terminal points (a), (a).

In addition, in the above potentiometric titration apparatus of the present invention, the control section (2) may be constructed so as to have a further computation function capable of displaying and preparing a titration curve and a differential curve on a display of the display/recording section (3) on the basis of the titration method defined by the conventional JIS method (JIS K0113), i.e., on the basis of the method using an inflection point, an intersection point and a differential curve, and to perform the titration procedure while changing-over the function of the control section to those of the JIS methods, if required. In this case, the analysis results of the titration method according to the present invention may be compared with the analysis results according to the conventional JIS method.

Meanwhile, in the potentiometric titration apparatus of the present invention, when executing the above algorithm, the titer and analysis results may be displayed on the display of the display/recording section (3) by numerals only. However, the titration curve or differential curve may also be graphed to display the respective estimation lines (B1) and (B2), intermediate line (C), intersection point (A) and terminal point (a), whereby the progress of titration and analysis results can be visually observed on the display.

FIGS. 5 and 6 represent images of titration analysis on the display as examples of the present invention. FIG. 5 shows a displayed image of oxidation-reduction reaction in which a Mohr's salt was titrated with $KMnO_4$, whereas FIG. 6 shows a displayed image of analysis for purity of caffeine in which anhydrous caffeine was titrated with an acetic acid solution of perchloric acid. In the example shown in FIG. 5, the titration curve prepared undergoes a large change in indicator potential in an inflection point portion thereof.

In accordance with the present invention, three or more measured points that are present on respective portions of the estimated titration curve which are spaced by a sufficient distance apart from an inflection point thereof and exhibit a moderate change in indicator potential, are used as decision points to obtain linear estimation lines on the respective curve portions by a least squares method, and an intersection point between an intermediate line of these estimation lines and the titration curve is determined as a terminal point of the titration. Therefore, according to the present invention, it is possible to accurately determine the terminal point of the titration without undergoing adverse influence owing to large change in indicator potential in the vicinity of the inflection point. Moreover, the present invention can be suitably applied to automatic titration, because the computation therefor can be readily carried out according to a program set previously.

What is claimed is:

1. A potentiometric titration method for conducting titration based on an amount of a titrant added and an indicator potential, said method comprising:

calculating a continuous line prepared by plotting a value (Y) of the indicator potential on an ordinate axis and plotting a value (X) of a volume of the titrant on an abscissa axis, as a titration curve, the values (X) and (Y) being determined according to the titration procedure;

calculating a continuous line prepared by plotting an absolute value of a rate of change in potential (dY/dX) on an ordinate axis and plotting the value (X) of a volume of the titrant on an abscissa axis, as a differential curve;

calculating a value on the titration curve which corresponds to a peak (P1) on the differential curve, as a tentative terminal point (P);

computing, on a computer, a straight line (D) connecting two measured values on the titration curve which are present adjacent to the tentative terminal point (P);

computing, on a computer, a linear first estimation line (B1) by a least squares method based on measured values (d1), (d2) and (d3) on the titration curve which are present in the range of from [(tentative terminal point (P))−(number of decision points (n))] to [(tentative terminal point (P))−(number of decision points (n))+2], and computing a linear second estimation line (B2) by a least squares method based on measured values (d4), (d5) and (d6) on the titration curve which are present in the range of from [(tentative terminal point (P))+(number of decision points (n))−2] to [(tentative terminal point (P))+(number of decision points (n))] wherein the number of decision points (n) represents the number of the measured values on portions of the titration curve previously set and used for determination of a terminal point of the titration, with the proviso that the number of the measured values are not less than 3 in each of the portions of the titration curve which extend in positive and negative directions, respectively, along the abscissa axis, on the basis of the tentative terminal point (P) as a reference point;

computing, on a computer, an intermediate line (C) between the first estimation line (B1) and the second estimation line (B2); and computing, on a computer, an intersection point (A) of the intermediate line (C) and the straight line (D) to read out a value of the intersection point on the abscissa axis as a terminal point (a) of the titration.

2. A potentiometric titration method according to claim 1, wherein a value on the titration curve corresponding to the peak (P1) on the differential curve at which the rate of change in potential (dY/dX) becomes maximum is calculated as the tentative terminal point (P).

3. A potentiometric titration method wherein a range of the value (Y) of indicator potential is divided into a plurality of regions (V1), (V2), . . . to each of which the method as defined in claim 1 is applied, to obtain a plurality of terminal points (a), (a), . . . .

4. A potentiometric titration apparatus comprising a titration vessel accommodating a sample, a detector for detecting a indicator potential using an indicator electrode and a reference electrode, a titration section constituted from a titrant addition device for adding a titrant to the sample, and a control section for controlling the titrant addition device based on the indicator potential detected by the detector and computing a terminal point of titration, wherein the control section has a function of computing the terminal point of titration according to the potentiometric titration method as defined in claim 1.

* * * * *